United States Patent [19]

Wasserman et al.

[11] 4,190,579

[45] Feb. 26, 1980

[54] SYNTHESIS OF BETA-LACTAMS FROM AZETIDINE CARBOXYLIC ACID ESTERS

[75] Inventors: Harry H. Wasserman, New Haven, Conn.; Bruce H. Lipshutz, Yonkers, N.Y.; James S. Wu, New Haven, Conn.

[73] Assignee: Research Corporation, New York, N.Y.

[21] Appl. No.: 865,593

[22] Filed: Dec. 29, 1977

[51] Int. Cl.$^2$ .................. C07D 205/08; C07D 403/06; C07D 409/06; C07D 407/06
[52] U.S. Cl. ............................. 260/239 A; 260/340.7; 260/340.9 R; 260/330.3; 260/326.13 B; 260/687 R
[58] Field of Search ....... 260/239 AL, 340.7, 340.9 R

[56] References Cited

FOREIGN PATENT DOCUMENTS

1914386 10/1970 Fed. Rep. of Germany ... 260/239 AL

OTHER PUBLICATIONS

Foote et al., Tet. Letters 1968, pp. 3267–3270.
Haber, Tet. Letters, 1968, pp. 3271–3272.
Foote et al., Tet. Letters, 1975, pp. 1247–1250.

*Primary Examiner*—Mark L. Berch
*Attorney, Agent, or Firm*—Haight & Huard

[57] ABSTRACT

Azetidine carboxylic acid esters are converted into enol silyl ethers which, as enamino ketene acetals, undergo ready oxidative cleavage of the ethylenically unsaturated double bond, e.g. by dye-sensitized photo-oxygenation, to form beta-lactams. The beta-lactams and substitution products thereof are useful intermediates in the synthesis of biologically active lactams.

7 Claims, No Drawings

SYNTHESIS OF BETA-LACTAMS FROM AZETIDINE CARBOXYLIC ACID ESTERS

CROSS-REFERENCE TO RELATED APPLICATIONS

A method for preparing beta-lactams from azetidine carboxylic acid starting materials via low temperature dianion oxygenation is described in copending, commonly assigned U.S. Patent application Ser. No. 736,343 filed Oct. 28, 1976, the contents of which are incorporated by reference herein.

A method for preparing beta-lactams from azetidine carboxylic acid starting materials via a decarbonylationperacid oxidation sequence involving the formation of iminium salts is described in copending, commonly assigned U.S. Patent application Ser. No. 831,441 filed Sept. 8, 1977, the contents of which are incorporated by reference herein.

BACKGROUND OF THE INVENTION

This invention was supported in part by Grants GM-07874 and GM-13854 from the National Institutes of Health, U.S. Public Health Service.

This invention relates to a process for the conversion of azetidine carboxylic acid esters into corresponding beta-lactams, to intermediates useful in the synthesis of biologically active beta-lactams and to methods for the synthesis thereof.

Beta-lactams have received increasing study as an essential component in several families of compounds having useful biological, especially antibacterial, activity, e.g. the beta-lactam-thiazolidine ring (penam) system common to all penicillins and the beta-lactam-dihydrothiazine (cepham) nucleus common to the cephalosporins, and increasingly in monocyclic beta-lactams which have been recently described. For example, Hashimoto et al. in J.A.C.S. 98(10): 3023 (May 12, 1976), have described the structure of nocardicin, a monocyclic beta-lactam having antibacterial activity. A number of additional monocyclic beta-lactams, many of which are structurally similar to the bicyclic penicillins and cephalosporins, have been described in Belgium Pat. No. 830,934 and by Bose et al. in J. Med. Chem. 17(4): 541 (1974).

At present, most monocyclic beta-lactams are synthesized by the reaction devised by A. K. Bose wherein azidoacetyl chloride is reacted with a Schiff base to form the beta-lactam. While in general a satisfactory technique, the azidoacetyl chloride reagent is relatively expensive and dangerous to work with in large quantities due to the risk of explosions. In particular, this method is not generally useful in the preparation of 4-unsubstituted beta-lactams.

Accordingly, particularly in view of the increasing research being directed to the preparation of biologically active beta-lactams and the use of beta-lactam intermediates in the synthesis of valuable antibacterial compounds such as the penicillins, cephalosporins, nocardicins, etc., there is need for a safe and inexpensive method for the preparation of beta-lactams and related intermediates.

The aforementioned copending U.S. Patent application Ser. No. 736,343 describes a low temperature dianion oxygenation process first reported by Wasserman and Lipshutz in Tetrahedron Letters: 4613 (1976) for the preparation of beta-lactams from azetidine-2-carboxylic acid starting materials. The aforementioned copending U.S. Patent application Ser. No. 831,441 describes an oxidative decarbonylation process utilizing iminium salt formation first reported by Wasserman and Tremper in Tetrahedron Letters 17: 1449 (1977) which employs the reactivity of iminium salts toward nucleophiles and extended the earlier process to be applicable to lactam formation in the presence of active (e.g. benzylic) hydrogen atoms in the substituent attached to the lactam ring nitrogen atom, which is not feasible in the earlier low temperature dianion oxygenation process.

While both of these earlier methods are suited for their intended purpose, there is still a need for a method which can be employed in the presence of active hydrogen atoms, which does not require the strongly acidic reaction conditions such as oxalyl chloride and peracid employed in the previous iminium salt method, and which can take place at the azetidine ester stage, and the present invention provides such a process.

OBJECTS OF THE INVENTION

Accordingly, it is a general object of the present invention to provide a method for the conversion of azetidine carboxylic acid esters to the corresponding beta-lactams, as well as monoanion and enamino ketene acetal intermediates useful in such a method.

Another object of the present invention is to provide a method for substituting the nitrogen atom of the lactam ring with a group bearing a benzylic or allylic hydrogen atom thereon, e.g. in the beta position.

A further object of the present invention is to provide beta-lactam derivatives which are useful as intermediates in the synthesis of biologically active lactams.

Upon study of the specification and appended claims, further objects, features and advantages of this invention will become apparent to those skilled in the art.

SUMMARY OF THE INVENTION

Briefly, the above and other objects, features and advantages of the present invention are attained in one aspect thereof by providing a process for preparing a cyclic lactam which comprises subjecting an amino carboxylic acid ester of the general Formula I:

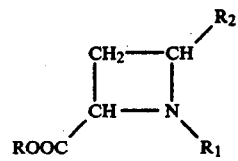

wherein
$R_2$ is hydrogen or alkyl of 1–6 carbon atoms;
$R_1$ is aliphatic or cycloaliphatic of up to ten carbon atoms optionally interrupted by a sulfur or oxygen atom, or hydrocarbon aryl, alkaryl or aralkyl of 6–10 ring carbon atoms and 1–6 alkyl carbon atoms wherein $R_1$ is unsubstituted or substituted 1–3 times by at least one member selected from the group consisting of alkyl of 1–4 carbon atoms, alkoxy of 1–4 carbon atoms, $-(CH_2)_nR'R''$ and $-NR'R''$ wherein n is a positive integer of 1–10, preferably 1–3, and wherein R' and R'' are each alkyl of 1–6 carbon atoms or collectively form a heterocyclic ring which is no more basic than imidazolyl and which contains 5–10 ring members and 1–3 nitrogen, oxygen or sulfur atoms, each of said members being unsubstituted or monosubstituted by alkyl of 1–4 carbon atoms or alkoxy of 1–4 carbon atoms, or R₁ is an allylic group of the formula —CHR₁'CH=CHR₂ or a benzylic group of the formula —CHR₁'—phenyl—p—R₂ wherein R₁' has the values given for R₁ and n, R₂, R' and R" have the above-indicated values; and R independently has the above-indicated values for R₁ to monoanion formation with a strong base to form a corresponding monoanion of the general Formula II:

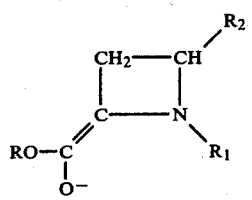

wherein R, R₁ and R₂ have the above-indicated values.

In another aspect, the present invention provides novel N-substituted enamino ketene acetals by O-silylation of a monoanion of Formula II to form the corresponding O-silyl enolate of the general Formula III:

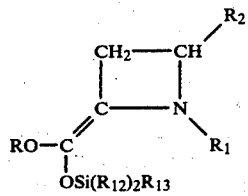

wherein R₁₂ and R₁₃ are each alkyl, phenyl, phenylalkyl, alkylphenyl or alkylphenylalkyl of 1–4 carbon atoms in the alkyl substituent.

In a third aspect, the present invention provides a method for the oxidation, e.g. by dye-sensitized photooxygenation, of an O-silyl enolate of Formula III into a corresponding beta-lactam of the general Formula IV:

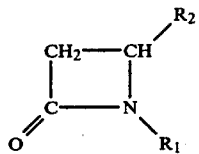

In a fourth aspect, the present invention provides a method for the synthesis of biologically active beta-lactams, particularly those containing a benzylic or allylic hydrogen atom in the substitutent on the lactam nitrogen atom.

DETAILED DISCUSSION

In one aspect of the present invention, it has been found that alpha-carboxylic acid ester derivatives of cyclic amines having the general Formula I

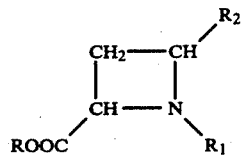

wherein R, R₁ and R₂ are as defined herein can undergo monoanion formation followed by O-silylation of the monoanion to form an enamino ketene acetal which can then be oxidized to form a corresponding beta-lactam.

The starting materials of Formula I are readily available or can be prepared according to methods described in the aforementioned copending U.S. Patent application Ser. No. 736,343 or described in the literature, e.g. see Cromwell et al., J. Hetero. Chem. 6:435 (1969). The ester group R can be introduced by any of the conventional esterification techniques known to those skilled in the art.

While not wishing to be bound by any theory of the invention, it is believed that conversion of the azetidine carboxylic acid ester I involves the formation of an intermediate monoanion thereof II which reacts readily with a trialkyl silyl halide to form the intermediate enamino ketene acetal III which can then be oxidized to form the corresponding lactam IV. R in this reaction scheme is the residue of any carboxylic acid ester meeting the criteria defined hereinafter.

R₁ in the above reaction scheme can be any organic residue having a carbon atom covalently bonded to the azetidine ring nitrogen atom which does not interfere with monoanion and O-silyl enolate formation or the subsequent oxygenation thereof to form the desired beta-lactam product. R₁ values meeting the above criteria can be aliphatic, cycloaliphatic, hydrocarbon aromatic and hydrocarbon, heteroatomic or heterocyclic containing one or more nitrogen, oxygen and/or sulfur atoms as defined below.

Aliphatic or cycloaliphatic is preferably of up to six carbon atoms, e.g., alkyl, alkenyl, alkynyl, cycloalkyl or cycloalkenyl. Suitable alkyl groups include but are not limited to methyl, ethyl, n-propyl, isopropyl, n-butyl, isobutyl, sec.-butyl and tert.-butyl. Suitable alkenyl groups include but are not limited to vinyl, 2,2-dimethylvinyl, allyl, dimethylallyl, 1-propenyl, 1-butenyl, 2-butenyl, 3-meththyl-2-butenyl, 1-pentenyl and 2-pentenyl. Suitable alkynyl groups include but are not limited to propynyl, butynyl and pentynyl. Suitable cycloalkyl groups include but are not limited to cyclopropyl, cyclobutyl, cyclopentyl and cyclohexyl optionally substituted, e.g., by alkyl or alkenyl of up to four carbon atoms to form cycloalkylalkyl or cycloalkylalkenyl, e.g., cyclopropylmethyl. Suitable cycloalkenyl groups include but are not limited to cyclobutenyl, cyclopentenyl and cyclohexenyl optionally substituted e.g., by alkyl or alkenyl of up to four carbon atoms to form cycloalkenylalkyl or cycloalkenylalkenyl, e.g., cyclobutenylethyl.

Hydrocarbon aromatic can be aryl, alkaryl, aralkyl, alkarylalkyl or aralkenyl wherein alkyl and alkenyl each have the above-indicated values. Hydrocarbon aryl is preferably phenyl, naphthyl or substituted phenyl; hydrocarbon alkaryl is preferably alkylphenyl or substituted alkylphenyl, e.g., tolyl; hydrocarbon aralkyl is preferably phenylalkyl or substituted phenylalkyl of 1–4 carbon atoms in the alkyl substitutent, e.g., benzyl or phenylethyl; and hydrocarbon alkarylalkyl is preferably lower alkyl-phenyl-lower alkyl which can be unsubstituted or substituted as defined herein, e.g. methylbenzyl. Suitable substituents of the hydrocarbon aromatic group are 1–3 lower alkyl groups, e.g., methyl; 1–3 lower alkoxy groups, e.g., methoxy or ethoxy; and 1–3 halogen atoms, e.g., fluorine, chlorine or bromine. Suitable substituted hydrocarbon aromatic groups include but are not limited to o-, m- or p-tolyl, o-, m- or p-methoxyphenyl, o-, m- or p-fluorophenyl, o-, m- or p-chlorophenyl and alpha- or beta-naphthyl. Aralkenyl is preferably phenylalkenyl of 2-6 carbon atoms in the alkenyl substituent, e.g., phenylallyl.

$R_1$ can be a group of the formula $-(CH_2)_n R'R''$ wherein n has the above-indicated values and $R'$ and $R''$ are each alkyl of 1-6 carbon atoms, aryl, aralkyl or alkaryl of 6-10 carbon atoms each of which is unsubstituted or substituted by 1-3 alkoxy of 1-4 carbon atoms or by a single heterocyclic ring of 4-7 members containing a total of 1-3 nitrogen, oxygen or sulfur atoms; or $R'$ or $R''$, collectively represent a monovalent heterocyclic or hydrocarbon ring which can be unsubstituted or substituted by 1-3 alkyl of 1-4 carbon atoms or alkoxy of 1-4 carbon atoms.

Monovalent heterocyclic ring substituents encompassed by the present invention are generally of 5-10, preferably 5 or 6 ring atoms of which 1-4, generally 1-3 and preferably 1 or 2, are oxygen, nitrogen and/or sulfur heteroatoms. The heterocyclic ring can be nonhydrogenated, e.g., imidazolyl, thiazolyl, etc.; partially hydrogenated, e.g., imidazolinyl, oxazolinyl, thiazolinyl, etc.; or completely hydrogenated, e.g., piperazinyl, morpholino, tetrahydropyrimidinyl, etc.

Suitable heterocyclic groups can be those derived from a five member heterocyclic ring containing a single heteroatom, e.g., furyl, thienyl or pyrrolyl; a five member heterocyclic ring containing two heteroatoms, e.g., pyrazolyl, imidazolyl, oxazolyl, oxazolinyl, isoxazolyl, isoxazolinyl, thiazolyl or thiazolinyl; a five member heterocyclic ring containing three heteroatoms, e.g., triazolyl, oxadiazolyl, thiadiazolyl, dioxazolyl and oxathiazolyl; or a five member heterocyclic ring containing four heteroatoms, e.g., tetrazolyl, oxatriazolyl and thiatriazolyl. Preferred heterocyclic groups derived from a five member heterocyclic ring are furyl, thienyl, pyrrolyl, pyrazolyl, imidazolyl, isoxazolyl and thiazolyl, especially thienyl.

Suitable heterocyclic groups can also be those derived from a six member heterocyclic ring containing a single heteroatom, e.g., pyridyl, pyranyl and thiopyranyl, preferably pyridyl; a six member heterocyclic ring containing two ring heteroatoms, e.g., dioxinyl, pyridazinyl, pyrimidinyl, pyrazinyl, piperazinyl, oxazinyl and morpholino, preferably pyridazinyl, pyrimidinyl, piperazinyl or morpholino; or a six member heterocyclic ring containing three ring heteroatoms, e.g., triazinyl, oxathiazinyl and oxadiazinyl. Preferred heterocyclic groups derived from a six member heterocyclic ring are pyridyl, pyridazinyl, pyrimidinyl, piperazinyl and morpholino.

Suitable heterocyclic groups can furthermore be those derived from a fused heterocyclic ring containing one six-membered ring fused to a five-membered ring wherein the six-membered ring is preferably alicyclic but can be interrupted by a single oxygen or nitrogen atom and wherein the five-membered ring contains one or two, preferably one, oxygen, nitrogen or sulfur heteroatoms, e.g., indolyl.

Presently preferred heterocyclic ring values for $R_1$ are furyl, thienyl, pyrrolyl, oxazolyl, imidazolyl and indolyl.

$R_2$ in the above formulae is preferably hydrogen but can also be lower alkyl of 1-6, preferably 1-3, carbon atoms, e.g. methyl, ethyl, n-propyl or isopropyl.

Where substitution is indicated for any radical on compounds in accordance with the present invention, the degree of substitution unless otherwise indicated is generally 1-3, preferably 1 or 2, and it will be appreciated that potentially limiting factors such as steric hindrance and the like will be taken into account by those skilled in the art to which this invention pertains. So that the activity and characteristic structure of the compounds of Formula III is predominantly that of an enamino ketene acetal, the sum of the molecular weights of the substituents thereon is generally less than about 300, preferably less than about 200, and these substituents generally contain a total of not more than 15, preferably not more than ten carbon atoms and generally not more than five, preferably not more than three, heteroatoms. The compounds can optionally be of the general Formula V:

$$\begin{array}{c} R_3 \diagdown \quad \diagup R_2 \\ CH \!\!-\!\! CH \\ | \quad\quad | \\ -C \!\!-\!\! N \\ | \quad\quad \diagdown R_1 \end{array} \quad V$$

wherein $R_1$ and $R_2$ have the above-indicated values and $R_3$ is preferably hydrogen but can also be any of the values defined herein for $R_2$; these values can be introduced during formation of the azetidine carboxylic acid ester starting material of Formula I, e.g. in accordance with the methods of said copending U.S. Patent application.

Details for preparing compounds of Formula I wherein $R_1$ has the above-indicated values can likewise be found in the aforementioned copending U.S. Patent application Ser. No. 736,343.

A limitation in the process described therein is that the $R_1$ substituent cannot contain a benzylic or allylic hydrogen atom on the carbon atom which is covalently bonded to the lactam ring nitrogen atom, since this would be abstracted during dianion formation. This prior limitation is inapplicable to the reaction mechanism of the present invention so that $R_1$ can now include compounds which contain such a benzylic or allylic hydrogen atom, e.g. allyl or benzyl groups; such compounds are prepared analogously to those compounds of Formula I described in said copending application.

The $R_1$ groups which may now be incorporated into the lactam ring accordingly can now include those containing allylic or benzylic hydrogens on the carbon atom which is covalently bonded to the lactam ring nitrogen atom, e.g.,

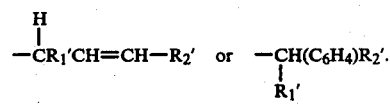

All of these active hydrogen atoms would have been removed in the earlier dianion oxygenation process but are not so subject to removal in accordance with the process of the present invention.

The azetidine carboxylic acid ester starting materials of Formula I can be converted into the corresponding monoanions of Formula II by techniques well known to those skilled in the art and under a wide variety of reaction conditions. However, it is preferable that a polar, aprotic solvent or solvent mixture be employed in order to effect dissolution of the intermediate monoanion species. Suitable such solvents are well known in the art and include but are not limited to THF (tetrahydrofuran), HMPA (hexamethylphosphoramide), diethylether, etc., either alone or in combination.

Aside from the use of a suitable solvent, the formation of the monoanion intermediate requires specific precautionary measures known to those skilled in the art. The reaction must be conducted in an inert atmosphere, e.g., nitrogen, argon, neon, helium, etc., preferably nitrogen or argon, and the inert atmosphere should be maintained at all times. Equipment should be scrupulously dried by heating prior to use so as to remove moisture to below tolerable levels. Choice of the strong base employed to form the monoanion must be such that the compound chosen is sufficiently basic with respect to the proton to be abstracted as well as being non-nucleophilic. Generally, bases in which the corresponding conjugate acid has a pKa equal to or greater than 19, preferably greater than 26, are suitable for proton abstraction from a large number of azetidine carboxylic acid esters. Such bases include but are not limited to KO—C(CH$_3$)$_3$, Li—NCH(CH$_3$)$_2$C$_6$H$_{11}$, Li—N(C$_6$H$_{11}$)$_2$, Li—N(C$_6$H$_5$)$_2$, LiC$_6$H$_5$, Li—N(Me$_3$-Si)$_2$, Li—N[CH(CH$_3$)$_2$]$_2$ (LDA), etc., with the use of the latter preferred.

The corresponding aminocarboxylic acid ester of Formula I is reacted, e.g. at $-78°$ C., with a base which is sufficiently strong to abstract a proton from the carboxyl group to form the intermediate monoanion of Formula II. Reaction temperatures and pressures are conventional and can range from $-90°$ C. or lower to room temperature or higher at atmospheric pressure. At ambient pressures, temperatures ranging from $-90°$ C. to the boiling point of the lowest boiling component of the solvent system employed can be used. The preferred temperature range is $-90°$ C. to $-70°$ C. at atmospheric pressure, and the reaction proceeds well at these temperatures. However, higher or lower temperatures can be employed depending upon the pressure under which the reaction is conducted.

The monoanions of Formula II are not usually isolated but qualitatively confirmed, e.g. by the use of nuclear magnetic resonance or infrared spectroscopy. These intermediates can, if desired, be isolated by simple removal of volatile materials in vacuo.

Silyl formation can be effected by several techniques known in the art. The enolates formed by reaction of the monoanion with a strong base in general react readily with trialkyl halosilanes, preferably chlorosilanes, to form the enamino O-silyl ketene acetals. Suitable silanes are those which can be successfully used to mask hydroxyl groups and are well known in the art. Such silanes include but are not limited to trialkyl chlorosilanes, preferably wherein each of the alkyl groups is independently of 1-4 carbon atoms, especially tert-butyldimethylchlorosilane.

The formation of the beta-lactam IV via oxidative cleavage of the enamino ketene acetal is effected by treatment with an oxidizing agent which is sufficiently strong to cleave the ketene acetal and form a carbonyl group at the same position in the lactam ring; singlet oxygen has the advantage of favoring beta-lactams as the only isolatable products, presumably via cleavage of a dioxetane intermediate. Use of strong oxidizing agents such as ozone resulted in lower yields and the formation of further products as a result of additional oxidation and decomposition. For example, following the above procedures but using ozone instead of singlet oxygen in attempts to cleave the enamine double bond in the O-silyl ketene acetals, only about 10% of the desired lactam product was obtained, together with numerous other products resulting from further oxidation and decomposition. Accordingly, the preferred oxidizing agents are those which, while sufficiently strong to cleave the ketene acetal and form a carbonyl group at the same position in the lactam ring, are at the same time sufficiently weak so as not to further oxidize the particular beta-lactam product formed. The choice of an oxidizing agent for a particular application can of course vary widely within the above criteria.

A suitable general procedure employed is to form the monoanion intermediate by reaction with LDA and THF at $-78°$ C. to yield the enolate which reacts readily with tert-butyldimethylchlorosilane to form the enamino O-silyl ketene acetals. These enamino acetals need not be isolated, but can be allowed to react in situ with singlet oxygen. The beta-lactams form as the only isolatable products, presumably via cleavage of a dioxetane intermediate.

Suitable techniques for generating singlet oxygen for use in the above reaction are many and varied, e.g. see the book "Singlet Oxygen" edited by A. Paul Schapp and published by Dowden, Hutchinson & Ross, Inc., Stroudsburg, Pa. (1976), the contents of which are incorporated by reference herein.

The beta-lactam product can then be isolated and purified by conventional techniques, which will be chosen depending on the particular molecular structure and state of matter obtained. Solids or liquids can both be chromatographed on florisil or alumina, e.g., using chloroform-ether as an eluent; liquids can be kugelrohr-distilled under high vacuum.

Following the above procedure, the following compounds were obtained in the yields indicated below. Several of these examples are noteworthy in presenting cases which had not been amenable to the earlier dianion approach; it is significant that, although several of the esters contained an allylic or benzylic proton on the alpha-carbon atom of the residue attached to the lactam nitrogen ring, reaction with a single equivalent of LDA at $-78°$ C. still permits the selective abstraction of that labile proton. Following silylation, reaction with singlet oxygen yields the azetidinones.

| Beta-Lactam | R | (Yield, %) |
|---|---|---|
| ![CH$_2$—CH$_2$ ring with C(=O)—N—R (beta-lactam)] | —CH$_2$—(C$_6$H$_3$(OMe)$_2$)(MeO, MeO)—OMe | 56 |
| | —CH$_2$—CH=CH$_2$ | 48 |
| | —CH$_2$CH$_2$—(C$_6$H$_4$)—OMe | 66 |
| | —(thiophene-S) | 50 |
| | —CH$_2$CH(OCH$_3$)$_2$ | 56 |
| | —CH(C$_6$H$_5$)$_2$ | 55 |

When attempts were made to extend the silylation-oxidation sequence to 5- and 6-membered ring analogs, N-methylproline ethyl ester and N-methylpipecolinic acid ethyl ester, the expected lactam products were not formed. Instead, low yields of pyrrole and the alpha,beta-unsaturated ester, respectively, were isolated.

It will be appreciated that the process of the present invention provides a simple manner for preparing beta-lactams bearing a wide variety of substituents on the lactam nitrogen atom. In this connection, $R_1$ is preferably straight-chain or branched alkyl, e.g., methyl, ethyl, n-propyl, isopropyl, n-butyl, isobutyl, sec.-butyl, tert.-butyl, n-pentyl, isopentyl, n-hexyl, n-heptyl, n-octyl, 2-ethylhexyl, n-nonyl, n-decyl, n-undecyl, n-dodecyl, n-tridecyl or n-tetradecyl; alkenyl, e.g., allyl or crotyl; alkynyl, e.g., propargyl; alkoxyalkyl, e.g., 2-methoxyethyl or 2-ethoxyethyl; the above corresponding groups having an oxygen or sulfur atom in the chain; tertiary aminoalkyl, e.g., wherein the amino group is separated by at least two carbon atoms from the primary amine group, including N,N-dialkylaminoalkyl; cycloalkyl and cycloalkyl-alkyl primary amines, e.g. containing 3-8 ring carbon atoms, preferably 5 or 6, e.g., cyclopentyl, cyclohexyl, 2-cyclohexylethyl or 3-cyclohexylpropyl; azacycloalkyl, azacycloalkylalkyl and related cyclic groups, preferably containing a total of 5 or 6 ring members, with 1-2 of N and 0-1 of O or S as ring members in addition to ring carbon atoms and wherein the ring is at least one carbon removed from the amino group, e.g., by lower alkylene. Hydroxyl groups may lead to deleterious side reactions such as dehydration and polymerization and accordingly should be avoided.

Especially preferred as intermediates for subsequent synthesis of beta-lactam-containing compounds having pharmaceutical utility are those wherein the lactam nitrogen is substituted with an alkylene dialkoxy group of any desired chain length, preferably lower alkylene di-lower alkoxy of 1-8 carbon atoms in the alkyl group and 1-4 carbon atoms in each alkoxy group, e.g., ethylenedimethoxy. An additional preferred class of beta-lactams obtainable in accordance with the present invention is that wherein the lactam nitrogen is substituted by an alkenyl group of any desired chain length, preferably of 3-10 carbon atoms, in which the ethylenic unsaturation is spaced by at least one carbon atom from the lactam nitrogen, e.g., allyl. As with the acid-labile acetals, these alkenyl-substituted beta-lactams have latent functionality and facilitate expansion of the side chains to form a variety of end products.

Suitable alkenyl-substituted beta-lactams are formed from azetidine carboxylic acid esters in which $R_1$ is of the general Formula VI:

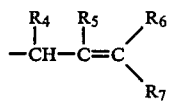

VI wherein $R_4$ has the above-indicated values for $R_1$, especially as in nocardicin, and $R_5$, $R_6$ and $R_7$ are each hydrogen or alkyl of 1-10, preferably 1-3, carbon atoms.

Suitable acetals are formed from azetidine carboxylic acid esters in which $R_1$ is of the general Formula VII:

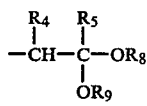

VII wherein $R_4$ and $R_5$ have the above-indicated values and $R_8$ and $R_9$ are each alkyl of 1-6 carbon atoms or $R_8$ and $R_9$, together with the oxygen atoms to which they are bonded, collectively form alkylenedioxy of 2-8 carbon atoms. Alkylenedioxy is preferably of 2-4 carbon atoms, e.g., ethylenedioxy, propylenedioxy, etc.

Substitution of the beta-lactam at the 3-position is readily accomplished according to techniques well known in the literature, e.g., see Kuhlein and Jensen, Liebigs Ann. Chem. 1974, pp. 369-402. As with the details of the iminium salt reactions, this can be achieved with a variety of reaction conditions. Preferred substituents at the 4-position of the lactam ring can be produced during ring formation; presently preferred are those substituents occurring at this position in the known active monocyclic beta-lactams, e.g., p-methoxyphenyl, o-nitrophenyl, o-aminophenyl, 1-(amidobenzyl)phenyl, 2-furanyl, p-carboxyphenyl and the like. Similarly, preferred substituents on the lactam nitrogen are those commonly occurring in antibacterially active monocyclic beta-lactams, e.g. p-acetylphenyl, diphenylmethylene, phenyl, p-methoxyphenyl, p-carboxyphenyl, p-carboxymethylphenyl and benzyl. An especially preferred substituent at the 3-position is the azide group $N_3$ because this group is readily reduced to the amino group $NH_2$, which in turn can be converted into a corresponding amide by suitable reaction with acid residues found in the penicillins and cephalosporins, e.g., phenylacetyl, phenoxyacetyl, 2-pentenoyl, n-pentanoyl, n-heptanoyl, p-hydroxyphenylacetyl, allythioacetyl, etc.

Compounds of this invention which contain a center of asymmetry are ordinarily obtained in the racemic form. The racemates can be separated into their optical antipodes in accordance with a plurality of known methods described in the literature; chemical separation is preferred. According to this procedure, diastereomers are formed from the racemic mixture by reaction with an optically active auxiliary agent. Thus, an optically active base can be reacted with the carboxyl group, or an optically active acid with the amino group, of a suitable compound of this invention. For example, diastereomeric salts of compounds containing a free carboxyl group can be formed with optically active amines, e.g., quinine, cinchonidine, brucine, hydroxyhydrindiamine, morphine, 1-phenylethylamine, 1-naphthylethylamine, phenyloxynaphthylmethylamine, quinidine and strychnine or basic amino acids, e.g., lysine, arginine and amino acid esters; or diastereomeric salts of basic compounds can be formed with optically active acids, e.g., (+)- and (—)- tartaric acid, dibenzoyl-(+)- and -(—)-tartaric acid, diacetyl-(+)- and -(—)-tartaric acid, camphoric acid, beta-camphorsulfonic acid, (+)- and (—)-mandelic acid, (+)- and (—)-malic acid, (+)- and (—)-2-phenylbutyric acid, (+)- and (—)-dinitrodiphenic acid or (+)- and (—)-lactic acid. In a similar manner, ester distereomers can be produced by the esterification of compounds containing a free carboxyl group with optically active alcohols, e.g., borneol, menthol or 2-octanol. The thus-obtained mixtures of diastereomeric salts and/or esters can be separated, e.g. by selective crystallization, and the desired optically active compounds can be produced by hydrolytic separation of the isolated diastereomeric compound.

Especially preferred compounds of the present invention are those of the above formulae in which one or more of the substituents thereon have the following preferred values:

(a) $R_1$ is alkyl or alkenyl of up to six carbon atoms which is unsubstituted or substituted as aforesaid and which is optionally interrupted by a sulfur atom;

(b) $R_1$ is alkyl, hydrocarbon aryl, alkaryl or aralkyl monosubstituted by $-NR'R''$;

(c) $R_1$ is alkenyl of the formula

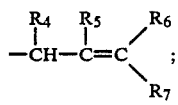

(d) $R_1$ is alkenyl of the formula

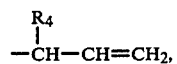

especially wherein $R_4$ is p-alkoxyphenyl or p-benzyloxyphenyl;

(e) $R_1$ is an acetal group of the formula

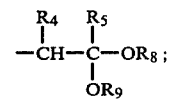

(f) $R_1$ is as in (e), wherein $R_4$ is p-alkoxyphenyl or p-benzyloxyphenyl;

(g) $R_2$ is hydrogen or alkyl of 1-3 carbon atoms, preferably hydrogen and especially as in (a) thru (f) inclusive;

(h) $R_3$ is alkyl of 1-4 carbon atoms, benzyl or benzhydryl, especially as in (a) thru (g) inclusive;

(i) $R_4$ is alkoxy, aryloxy, alkoxyaryl, aryloxyalkyl or aryloxyaryl, especially as in (g);

(j) $R_4$ is p-alkoxyphenyl or p-benzyloxyphenyl, especially as in (g);

(k) $R_5$ is hydrogen or alkyl of 1-3 carbon atoms, preferably hydrogen, especially as in (c) thru (j) inclusive;

(l) $R_6$ and $R_7$ are each hydrogen or alkyl of 1-3 carbon atoms, preferably hydrogen, especially as in (g) thru (k) inclusive;

(m) $R_8$ and $R_9$ are each alkyl of 1-3 carbon atoms, especially methyl or ethyl, or $R_8$ or $R_9$, together with the oxygen atoms to which they are bonded, form alkylenedioxy of 2-3 carbon atoms, especially as in (f) and (g) through (k) inclusive;

(n) enamino ketene acetals of the formula

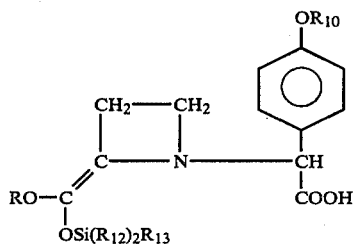

wherein $R_{12}$ and $R_{13}$ are each alkyl, phenyl, phenylalkyl, alkylphenyl or alkylphenylalkyl of 1-4 carbon atoms in the alkyl substituent and $R_{10}$ is a cleavable hydroxyl masking group, preferably alkyl, alkanoyl, aroyl, arylalkyl, alkylsulfonyl, arylsulfonyl or trialkylsilyl and especially alkyl of 1-4 carbon atoms, e.g. methyl, or benzyl or benzhydryl;

(o) enamino ketene acetals of the formula

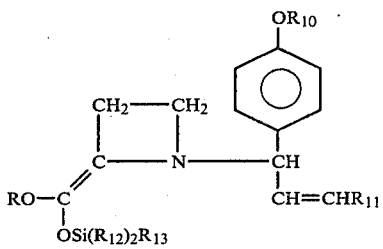

wherein $R_{10}$ $R_{12}$ and $R_{13}$ are each as defined in (n) and $R_{11}$ is hydrogen or alkyl of 1-6 carbon atoms, especially hydrogen;

(p) $R_1$ contains a heterocyclic ring as defined herein which is separated from the nitrogen atom to which $R_1$ is bonded by at least one carbon atom, e.g., by alkylene of 1-10, preferably 1-6, carbon atoms such as methylene, ethylene, n-propylene, etc., especially methylene and most especially as in (g) thru (m) inclusive; and (q) $R_1$ contains an hydrocarbon aryl, alkaryl or aralkyl ring as defined herein which is separated from the nitrogen atom to which $R_1$ is bonded by at least one carbon atom, e.g., by alkylene of 1-10, preferably 1-6, carbon atoms such as methylene, ethylene, n-propylene, etc., especially methylene and most especially as in (g) thru (m) inclusive. Particularly preferred such values for $R_1$ are benzyl or benzhydryl, either unsubstituted or substituted as defined herein.

The possibility provided by the cleavage of enol silylates of general formula III to beta-lactams in the presence of benzyl groups attached to nitrogen provides an opportunity of preparing key units in the synthesis of biologically active lactams.

Thus, as shown in the sequence below, the beta-lactam VIII containing a trimethoxybenzyl group attached to nitrogen can be converted to the 3-azido derivative IX by standard procedures (Kuhlein and Jensen, *Liebigs Ann. Chem.*, 1974, p. 369-402). Reduction and acylataion, as described in copending application 736,343, then leads to the 3-acylamino derivative X. Cleavage of the benzyl group either by standard hydrogenolysis or by the new oxidative method reported by Huffman et al. (J. Am. Chem. Soc., 99, 2352 (1977)) yields the parent 3-acylamino beta-lactam XI which can then be alkylated with the benzyl ester of alpha-bromo-p-benzyloxyphenylacetic acid (Belgium Pat. No. 830,934; see copending application No. 736,343) to yield the known precursor of 3-ANA XII.

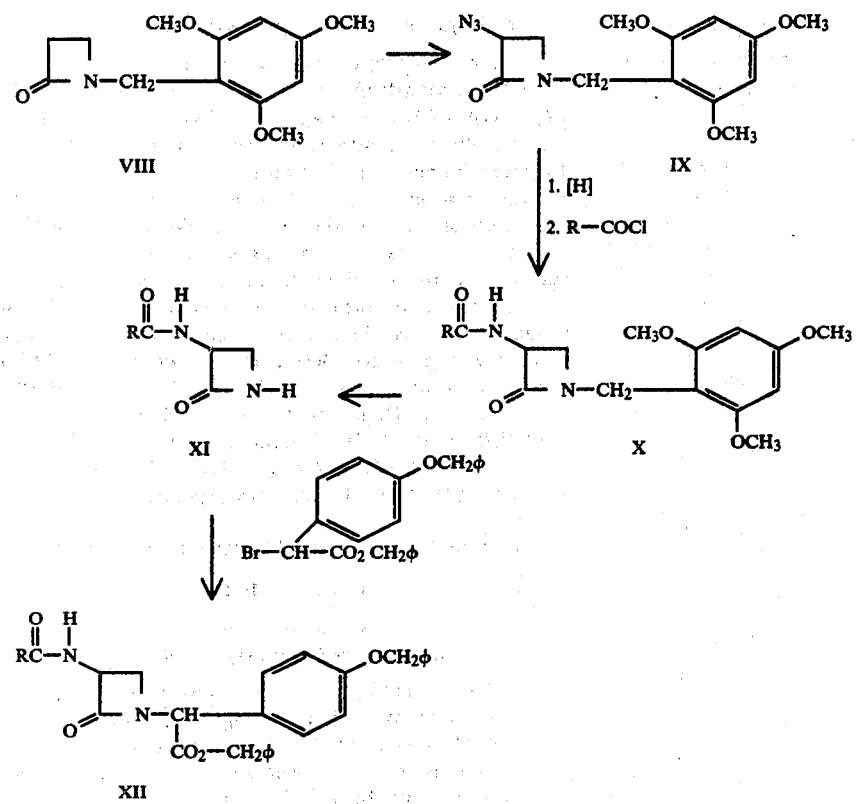

Specific compounds of the present invention, in addition to those shown above and in the following examples, include but are not limited to the following:

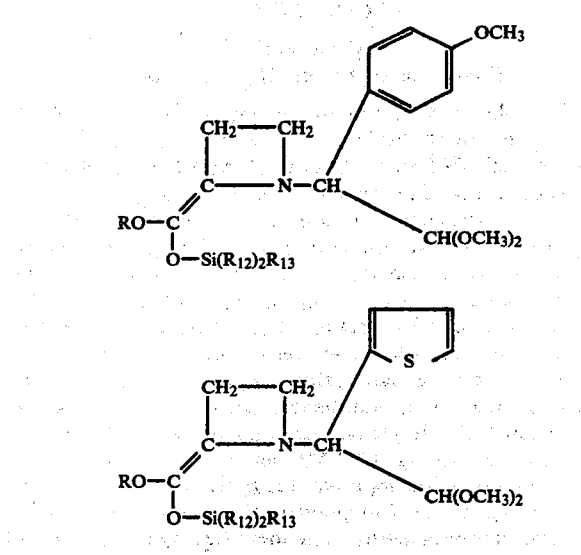

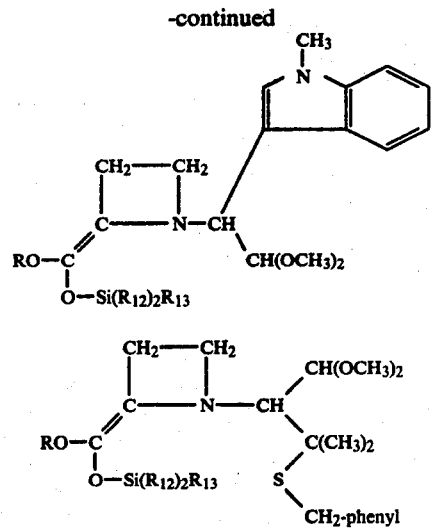

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. All temperatures are set forth uncorrected in° Celsius; unless otherwise indicated, all pressures are ambient and all parts and percentages are by weight. The values obtained by elemental analysis are within the usual limits of experimental error; all new products gave the expected parent peaks in the mass spectra and the expected absorption peaks in NMR and IR.

EXAMPLE 1

Preparation of N-tert-butyl-2-carbomethoxyazetidine

The procedure of Cromwell described in J. Heterocyclic Chem. 6: 435 (1969) and 5: 309 (1968) was followed for the preparation of this ester. To a 200 ml round bottom flask was added 5.20 g (0.02 mol) methyl 2,4-dibromobutyrate, 80 ml acetonitrile and 4.69 g (0.06 mol) of t-butylamine. After stirring at room temperature for 5 minutes, heat was applied and the temperature raised to and maintained at reflux for 24 hours. The yellowish mixture was cooled to room temperature and filtered. The filtrate was concentrated in vacuo, giving a yellow liquid to which dry ether was added. The pot was vigorously shaken and the ether solution decanted. This was repeated three times. The combined extracts were dried over anhydrous magnesium sulfate, filtered, and rotary evaporated to give a pale yellow liquid. Kugelrohr distillation at 65° (1.8 mm) afforded 2.3 g (70%) of a water-white liquid: IR (liquid film) cm$^{-1}$ 1750, 1725, 1275, 1230, 1200, 1175, 1130, 1060; NMR (CDCl$_3$) delta 3.70 (3H, s), 3.93 (1H, t, J=8 Hz), 3.15 (2H, m), 2.13 (2H, m), 0.93 (9H, s).

EXAMPLE 2

Preparation of N-benzhydryl-2-azetidinone

To a solution of lithium diisopropylamide (2.2 mmol) in ca. 15 ml tetrahydrofuran cooled to −78° was added, dropwise with stirring, 0.54 g (2 mmol) of N-benzhydryl-2-carboethoxyazetidine dissolved in 4 ml tetrahydrofuran. After stirring for 20 minutes at this temperature, 0.40 g (2.7 mmol) tert-butyldimethyl chlorosilane in 2 ml tetrahydrofuran was added dropwise to the orange solution over a 2 minute period. Stirring was continued at −78° for 5 minutes and the cooling bath was then removed. The solution was warmed slowly to 0° where it was maintained for 30 minutes, and then warmed to room temperature for 30 minutes with additional stirring. Photooxygenation included transferring the resulting solution to an oxygenation well containing Rose Bengal (10 mg) dissolved in 50 ml tetrahydrofuran. The solution was diluted with an equal volume of pentane, cooled to 0° and photooxygenated internally. Uptake of 1 equivalent (45 ml) of oxygen occurred over a 5 minute period. The solution was poured into 50 ml of a saturated ammonium chloride solution (pH 8), diluted and extracted several times with ether. The combined extracts were washed twice with saturated sodium chloride solution and dried over anhydrous sodium sulfate. Removal of solvents by filtration and rotary evaporation gave an orange oil which was applied to a 10×2 cm neutral alumina column packed as a slurry in hexane. Elution with 2:1 hexane-ethyl acetate gave 0.37 g of pale yellow oil, which by NMR analysis indicated a 55% yield of the desired beta-lactam. Crystallization of some of the product was effected by dissolving the oil in 0.5 ml of tetrahydrofuran and adding the solution dropwise to 100 ml of pentane cooled to −78°. Upon warming to room temperature, most of the white solid went back into solution. The small quantity of crystalline beta-lactam so obtained was dried under a high vacuum overnight: m.p. 63°-65°; IR (oil) cm$^{-1}$ 1740, 1380, 1250, 1050, 760, 700; NMR(CDCl$_3$) delta 7.25 (10H, m), 6.15 (1H, s), 3.17 (2H, t, J=4 Hz), 2.90 (2H, t, J=4 Hz); mass spectrum m/e 237 (M+).

Anal. Calcd. for C$_{16}$H$_{15}$NO: 237.1153. Found: 237.1162.

EXAMPLE 3

Preparation of N-(2-propenyl)-2-azetidinone

Lithium diisopropylamide (2.2 mmol), formed in 15 ml of dry tetrahydrofuran was cooled to −78°; and 0.34 g (2 mmol) of N-(2-propenyl)-2-carbo-tert-butoxyazetidine dissolved in 3 ml tetrahydrofuran was added via a dropping funnel over 2 minutes. After stirring for 30 minutes at room temperature, the orange solution appeared to undergo silylation as previously described. The resulting dark orange solution was photooxygenated in the usual manner, and the pink solution obtained was concentrated by rotary evaporation. The residue was kugelrohr distilled directly at 90° (0.5 mm) to give 0.28 g of colorless material, which by NMR analysis indicated a 48% yield (0.10 g) of the desired beta-lactam: IR (liquid film) cm$^{-1}$ 1740, 1250, 1200, 1040, 930; NMR (CDCl$_3$) delta 5.80 (1H, m) 5.23 (1H, m), 5.13 (1H, m), 3.82 (2H, d, J=7 Hz), 3.22 (2H, t, J=4 Hz), 2.93 (2H t, J=4 Hz); mass spectrum: m/e 111 (M+).

Anal. Calcd for C$_6$H$_9$NO: 111.0684. Found: 111.0675.

EXAMPLE 4

Preparation of N-(2,4,6-trimethoxybenzyl)-2-azetidinone

In a 50 ml round bottom 3-neck flask was prepared a solution of 1.2 mmol lithium diisopropylamide in ca. 10 ml tetrahydrofuran. To this clear, practically colorless solution cooled to −78°, was added 0.34 g (1 mmol) N-(2,4,6-trimethoxybenzyl)-2-carbo-tert-butoxyazetidine dissolved in 3 ml tetrahydrofuran. After stirring for 1 hour at this temperature, the golden-orange solution was silylated and photooxygenated in the usual manner. The resulting pink solution was then concentrated in vacuo and the residue applied to a 10×2 cm silica gel (Woelm) column. Elution with chloroform gave 0.14 g (56%) of pale yellow liquid, which by NMR analysis was greater than 90% pure: IR (liquid film) cm$^{-1}$ 1745, 1600, 1230, 1210, 1150, 1060, 1050, 950, 820; NMR (CDCl$_3$) delta 6.09 (2H, s), 4.36 (2H, s), 3.79 (6H, s), 3.75 (3H, s), 2.98 (2H, t, J=4 Hz), 2.74 (2H, t, J=4 Hz).

Anal. Calcd for C$_{13}$H$_{17}$NO$_4$: 251.1156. Found: 251.1176.

EXAMPLE 5

Preparation of N-(2-p-methoxyphenethyl)-2-azetidinone

To a solution of lithium diisopropylamine (2.2 mmol) in 15 ml tetrahydrofuran at −78° was added 0.58 g (2.0 mmol) of N-(2-p-methoxyphenethyl)-2-carboethoxyazetidine in 3 ml tetrahydrofuran. The orange enolate solution was stirred for 1 hour at this temperature and silylated as previously described. The bright yellow solution obtained was photooxygenated in the usual fashion and aqueous workup afforded a yellow oil. Application of the residue to a 15×2 cm neutral alumina column followed by elution with 1:1 ethyl acetate-hexane gave a light yellow liquid which was placed under a high vacuum to remove any trace of silyl by-products. A clear, light yellow liquid (0.27 g, 66%) was obtained, which by NMR analysis was greater than 90% pure. The impurity was a high boiling hydrocarbon having an absorption in the region delta 1.0–2.0. The product obtained was identified by comparison of its IR and NMR spectra with the spectra of a known authentic sample.

EXAMPLE 6

Preparation of N-cyclohexyl-2-azetidinone

In a 50 ml three neck flask was prepared 2.2 mmol lithium diisopropylamide in 15 ml tetrahydrofuran at 0°. The clear, practically colorless, solution was cooled to −78° and 0.42 g (2.0 mmol) of N-cyclohexyl-2-carbo-tert-butoxyazetidine dissolved in 3 ml tetrahydrofuran was added dropwise over 2 minutes. The yellow enolate was formed during 30 minutes at this temperature and then quenched with tert-butyldimethyl chlorosilane as previously described. The yellow solution obtained upon silylation was photooxygenated in the usual fashion. Standard aqueous workup gave, upon removal of ether in vacuo, a residue which was applied to a neutral alumina column packed with hexane and eluted with 1:1 hexane-ethyl acetate. Placement of the light yellow material obtained under a high vacuum gave pure beta-lactam (0.14 g, 46%). The spectral properties (IR, NMR) of this material were identical to those of a known authentic sample.

EXAMPLE 7

Preparation of N-(2,2-dimethoxyethyl)-2-azetidinone

To a solution of 2.2 mmol of lithium diisopropylamide in 15 ml tetrahydrofuran at −78° was added dropwise 0.43 g (2 mmol) of N-(2,2-dimethoxyethyl)-2-carbethoxy azetidine in 3 ml of tetrahydrofuran. After stirring at −78° for 30 minutes, the deep yellow anion was silylated in the usual way and warmed to room temperature. Removal of all volatiles by rotary evaporation with a high vacuum pump gave a purple residue which was redissolved in dichloromethane. Internal photooxidation using 5 g of Photox (trademark for photoconductive lead-free zinc oxides available from The New Jersey Zinc Co.) as the sensitizer required less than 5 minutes for oxygen uptake. The mixture was then filtered free of sensitizer and worked up by aqueous extraction in the usual manner. The pink residue obtained was applied to a 17×2 cm neutral alumina column. Elution with 10:3 ethyl acetate-hexane yielded 0.18 g (56%) of pale yellow liquid, which by NMR analysis was greater than 90% pure. Comparison of its spectral properties (IR, NMR) with those of an authentic known sample confirmed the identity of the product as the expected beta-lactam.

EXAMPLE 8

Preparation of sec-butyldimethylchlorosilane

This compound was prepared in a fashion analogous to that described in J.A.C.S. 94: 6190 (1972) for the preparation of tert-butyldimethylchlorosilane. Thus, 6.4 g (50 mmol) dichlorodiethylsilane was dissolved in 75 ml dry pentane and cooled to 0°. sec-Butyllithium (42 ml, 1.2 M, 50 mmol) in hexane was added over 30 minutes via a constant addition funnel and the mixture stirred for 24 hours at room temperature. Filtration of all salts through Celite was followed by concentration in vacuo to ca. 25 ml. Atmospheric distillation at 139° gave 4.6 g (61%) water-white liquid: IR (liquid film) cm$^{-1}$ 2960, 1460, 1260, 1000, 860, 840, 810, 780; NMR (CDCl$_3$) delta 1.13–0.84 (9H, m), 0.38 (6H, s).

Anal. Calcd. for $C_6H_{15}ClSi$: C, 48.00; H, 10.00. Found: C, 48.16; H, 9.99.

EXAMPLE 9

Comparison of Silylating Agents

A brief study was undertaken to determine the effect of other silylating reagents in this procedure. Using an azetidine ester of Formula I wherein R is tert-butyl, R$_1$ is p-methoxyphenylethyl and R$_2$ is hydrogen, three different silyl chlorides were substituted for tert-butyldimethylsilyl chloride: sec-butyl-, n-butyl and methyl groups were substituted for the tert-butyl group with the other alkyl groups being methyl in all cases. Qualitative results indicated that the yield of beta-lactam was highest utilizing tert-butyldimethylsilyl chloride, presumably because the other silylating agents, particularly trimethylsilyl chloride, result in increased amounts of C-silylation. The particular silylating agent will accordingly vary somewhat with the specific materials being treated, and optimum results can be achieved by a few simple preliminary experiments.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

What is claimed is:

1. A process for preparing a cyclic lactam which comprises oxidizing an enamine ketene acetal of the formula

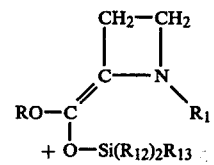

wherein

R and R$_1$ are each independently selected from the group consisting of:

(a) alkenyl of the formula

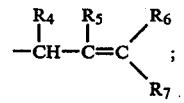

wherein R$_4$ is alkoxy, aryloxy, alkoxyaryl, aryloxyalkyl or aryloxyaryl, R$_5$ is hydrogen or alkyl of 1–3 carbon atoms and R$_6$ and R$_7$ are each hydrogen or alkyl of 1–3 carbon atoms;

(b) an acetal group of the formula

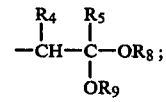

wherein R$_4$ and R$_5$ have the above-indicated values and R$_8$ and R$_9$ are each alkyl of 1–3 carbon atoms or R$_8$ or R$_9$, together with the oxygen atoms to which they are bonded, form alkylenedioxy of 2–3 carbon atoms;

$R_{12}$ and $R_{13}$ are each independently alkyl, phenyl, alkylphenyl, phenylalkyl or alkylphenylalkyl of 1–4 carbon atoms in each alkyl group with singlet oxygen to form a corresponding cyclic lactam of the formula:

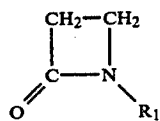

wherein $R_1$ has the above-indicated values.

2. A process according to claim 1, wherein $R_1$ is as in (a).

3. A process according to claim 1, wherein $R_5$, $R_6$ and $R_7$ are each hydrogen.

4. A process according to claim 1, wherein $R_4$ is p-alkoxyphenyl or p-benzyloxyphenyl.

5. A process according to claim 3, wherein $R_4$ is p-alkoxyphenyl or p-benzyloxyphenyl.

6. A process according to claim 1, wherein $R_1$ is as in (b).

7. A process according to claim 1, wherein said singlet oxygen is provided by photooxidation.